(12) United States Patent
Graw

(10) Patent No.: US 10,213,168 B2
(45) Date of Patent: Feb. 26, 2019

(54) RECLINING PATIENT CHAIR FOR NUCLEAR MEDICINE SYSTEM

(75) Inventor: Ansgar Graw, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2977 days.

(21) Appl. No.: 10/383,280

(22) Filed: Mar. 7, 2003

(65) Prior Publication Data

US 2004/0176676 A1 Sep. 9, 2004

(51) Int. Cl.
*G01T 1/00* (2006.01)
*G01T 1/166* (2006.01)
*A61B 6/04* (2006.01)
*A61G 15/02* (2006.01)

(52) U.S. Cl.
CPC .............. *A61B 6/0478* (2013.01); *A61B 6/04* (2013.01); *A61G 15/02* (2013.01)

(58) Field of Classification Search
USPC .... 5/601, 608, 609, 616, 617, 618; 600/407, 600/415, 425, 410, 421–422, 408, 436; 250/522.1; 378/193, 195–198, 208–209; 606/130; 297/311, 317, 319, 322, 325, 297/327, 337, 338
See application file for complete search history.

(56) References Cited

U.S. PATENT DOCUMENTS

| | | | | |
|---|---|---|---|---|
| 4,020,348 A * | 4/1977 | Turcotte et al. | ......... | 250/363.08 |
| 4,501,414 A * | 2/1985 | Mason et al. | ..................... | 5/614 |
| 4,862,529 A * | 9/1989 | Peck | ................................. | 5/611 |
| 5,008,624 A * | 4/1991 | Yoshida | ........................ | 324/318 |
| 5,042,487 A * | 8/1991 | Marquardt | .................... | 600/425 |
| 5,044,647 A * | 9/1991 | Patterson | ................... | 280/250.1 |
| 5,249,838 A * | 10/1993 | Kulpa et al. | .................. | 297/328 |
| 5,323,006 A * | 6/1994 | Thompson et al. | ..... | 250/363.02 |
| 5,342,114 A * | 8/1994 | Burke et al. | ............... | 297/344.2 |
| 5,386,453 A * | 1/1995 | Harrawood et al. | .......... | 378/196 |
| 5,594,251 A * | 1/1997 | Fleury et al. | ........... | 250/363.05 |
| 5,779,637 A * | 7/1998 | Palkovich et al. | ............ | 600/415 |
| 5,811,813 A * | 9/1998 | Maor | ....................... | 250/363.05 |
| 5,868,461 A * | 2/1999 | Brotherston | .................... | 297/84 |
| 6,217,214 B1* | 4/2001 | Cabral et al. | ................. | 378/196 |
| 6,373,060 B1* | 4/2002 | Yamakawa et al. | ..... | 250/363.08 |
| 6,374,133 B1* | 4/2002 | Dutto et al. | ................... | 600/415 |
| 6,377,830 B1* | 4/2002 | Carrozzi et al. | .............. | 600/407 |
| 6,455,856 B1* | 9/2002 | Gagnon | ................ | G01T 1/1644 250/363.03 |
| 6,522,145 B1* | 2/2003 | Damadian et al. | ........... | 324/318 |
| 6,567,997 B2* | 5/2003 | Harper | .............................. | 4/480 |
| 6,672,668 B1* | 1/2004 | Boruta et al. | ............ | 297/354.12 |
| 6,934,574 B1* | 8/2005 | Damadian et al. | .......... | 600/415 |
| 7,123,008 B1* | 10/2006 | Damadian et al. | ........... | 324/309 |
| 7,697,971 B1* | 4/2010 | Green et al. | .................. | 600/415 |

* cited by examiner

*Primary Examiner* — Patricia J Park

(57) ABSTRACT

A patient support for a nuclear medicine imaging system has a base a joint and a chair. The chair can pivot or rotate about the joint. This allows the patient chair to assume a patient loading and a patient imaging position with respect to the detectors of the imaging system. Furthermore, the chair is adjustable to improve the ability of a patient region to be covered by the filed of view of the detectors.

9 Claims, 9 Drawing Sheets

RECLINING PATIENT CHAIR FOR NUCLEAR MEDICINE SYSTEM

BACKGROUND

The invention relates to diagnostic imaging equipment, and more particularly relates to those parts of diagnostic imaging equipment that physically support the patient while the patient is undergoing an imaging study. In its most immediate sense, the invention relates to a patient handling system for use with nuclear medicine imaging equipment.

Nuclear medicine imaging assesses the radionuclide distribution within a patient after the in vivo administration of radiopharmaceuticals. The imaging systems that assess the radionuclide distribution comprise radiation detectors and associated electronics. The imaging systems detect x-ray or gamma ray photons derived from the administered radionuclides.

Many current nuclear medicine imaging systems often use a table or pallet to support the patient during scanning. This table presents a single fixed planar surface for the patient to lie upon. In general, during an imaging procedure, the medical practitioner performing the scan will start with the table in a loading position. The medical practitioner will place the patient upon the table. The medical practitioner will then move the table into an imaging position, often by moving the table into the field of view of a gamma camera in a detector attached to a gantry.

Many patients who require nuclear medicine imaging are infirm or otherwise physically debilitated. This can make placing, or loading, the patient onto a patient table difficult and painful for the patient, as well as time consuming for the medical practitioner performing the scan. As patient throughput is a determining factor in the economic viability of any medical scanning procedure, any technique of decreasing the time and difficulty of patient loading is advantageous.

Some newer nuclear medicine imaging systems utilize smaller gamma cameras specifically for cardiac nuclear medicine imaging. In some such systems, it may be preferable to have the patient sitting while the imaging occurs. Using a chair for patient support in a nuclear medicine imaging system reduces the total area, or footprint, required by the system. Furthermore, it is often much easier to load a patient onto a chair than a table. However, a sitting patient will sag and move in an upright sitting position, leading to a degraded image.

Thus, there remains a need in the field of nuclear medicine for a patient support that increases ease of patient loading while maintaining a low level of patient movement.

BRIEF DESCRIPTION OF THE DRAWINGS

The above description, as well as further objects, features and advantages of the present invention will be more fully understood with reference to the following detailed description of the preferred embodiments, when taken in conjunction with the accompanying drawings, wherein.

DETAILED DESCRIPTION

Figure 1:
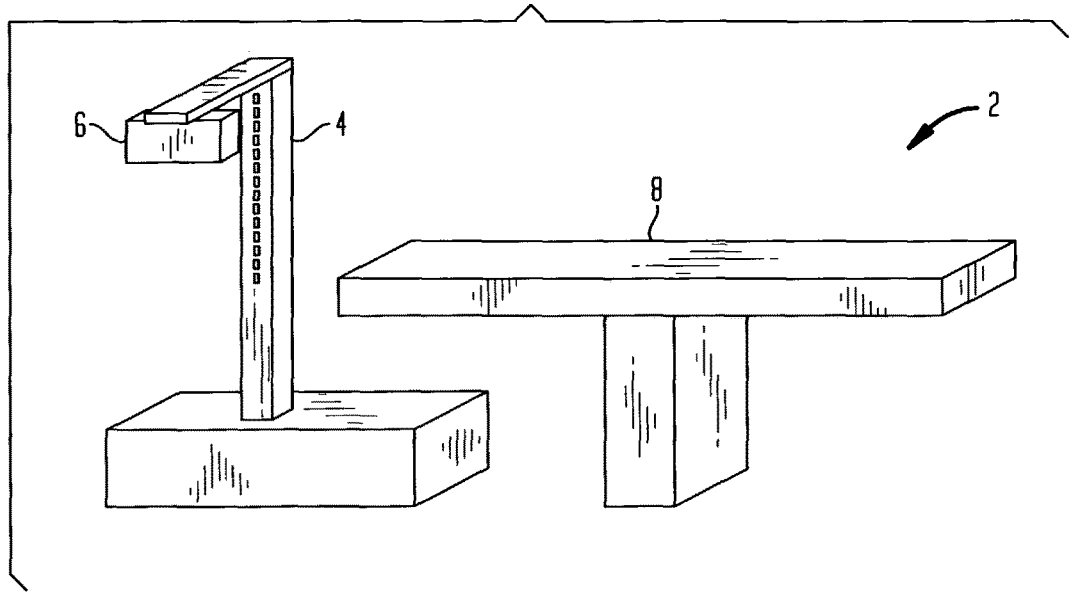
FIG. 1 is a side schematic view of a nuclear medicine imaging system with a table for patient support.

FIG. 1 shows a nuclear medicine imaging system 2 using a pallet-type patient support as described above. The nuclear medicine imaging system 2 includes a fixed gantry 4 and a detector 6 attached to the gantry 4. A patient table 8 is shown parallel to the floor. In operation, the patient table 8 will be positioned to be clear of the gantry 4 to allow a patient to be loaded onto table 8. This position is a patient loading position. System 2 is shown in FIG. 1 in a patient loading position. After a patient is loaded on the table 8, table 8 and the patient is moved into the field of view of the gamma camera within the detector 6. This is an imaging position of system 2 (not shown). Note that there are many possible imaging positions.

The detector 4 may move in reference to the gantry 6 via an arm or other device. This detector mobility allows other portions of the patient to be within the field of view of the gamma camera in detector 4.

Figure 2:
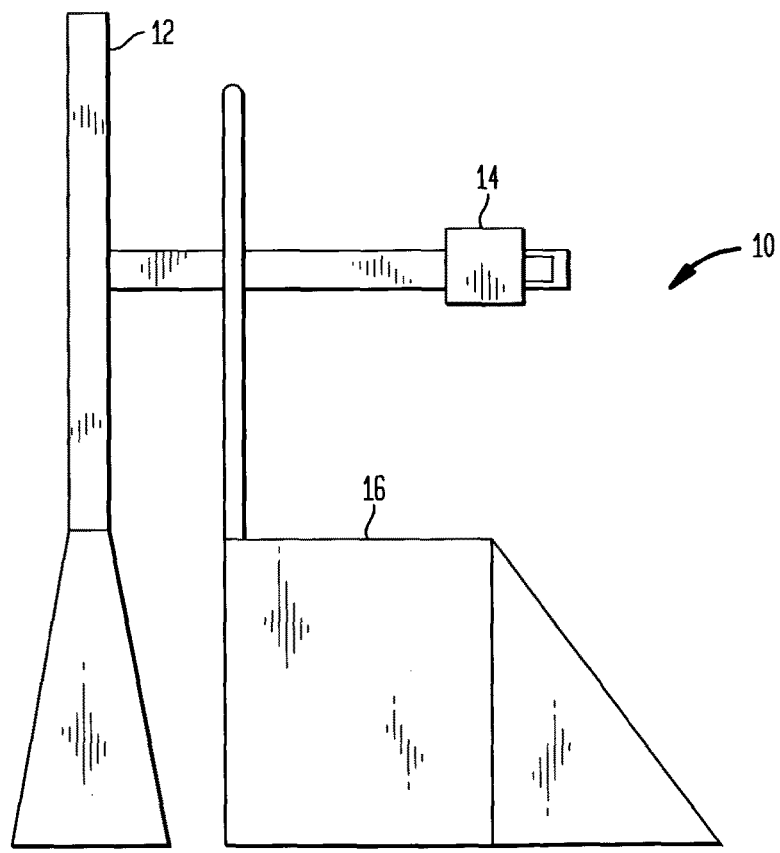
FIG. 2 is a side schematic view of a nuclear medicine imaging system with a chair for patient support.

FIG. 2 shows another nuclear medicine imaging system with a chair-type patient support as described above. The system 10 includes a gantry 12, a detector 14, and a patient chair 16. The detector is attached to the gantry 12. The chair 16 is fixed in relation to the gantry 12 in this embodiment. The detector 14 may move in relation to the gantry 12. In operation, the detector 14 is moved so that a patient may be loaded in the chair 16. The system 10 is shown with detector 14 in such a loading position. The detector 14 may then be moved such that the gamma camera's field of view covers a portion of the patient. This is an imaging position for system 10.

Figure 3:
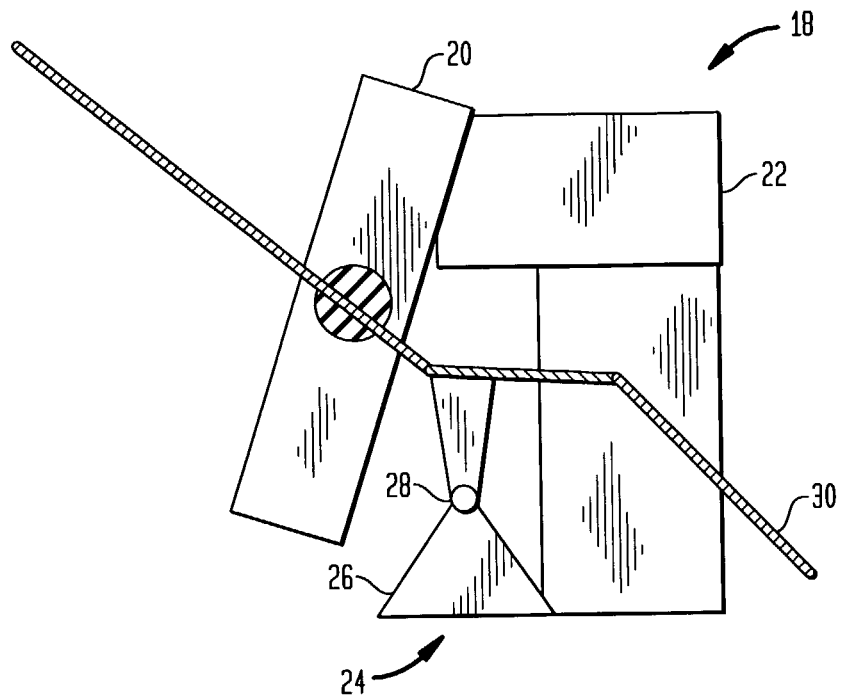
FIG. 3 is a side schematic view of an embodiment of the present invention.

FIG. 3 shows one embodiment of the present invention. A nuclear medicine imaging system 18 includes a detector 20, a gantry 22, and a patient support 24. The detector 20 is attached to the gantry 22. While FIG. 3 shows the detector 20 and the gantry 22 movable in relation to the patient support 24, they may also be fixed to the patient support 24. The patient support 24 comprises a base 26, a pivot 28, and a patient chair 30.

In operation, a medical technician may rotate the chair from a vertical (or upright) position to a more horizontal (or reclining) position. It is easier to load patients when the patient support 24 is in a more vertical position, and therefore this position may be called a loading position. FIG. 3 shows nuclear medicine imaging system 18 in its loading position. After loading, the chair may be rotated about pivot 28 to a more horizontal position that is more suitable for imaging.

Figure 4:
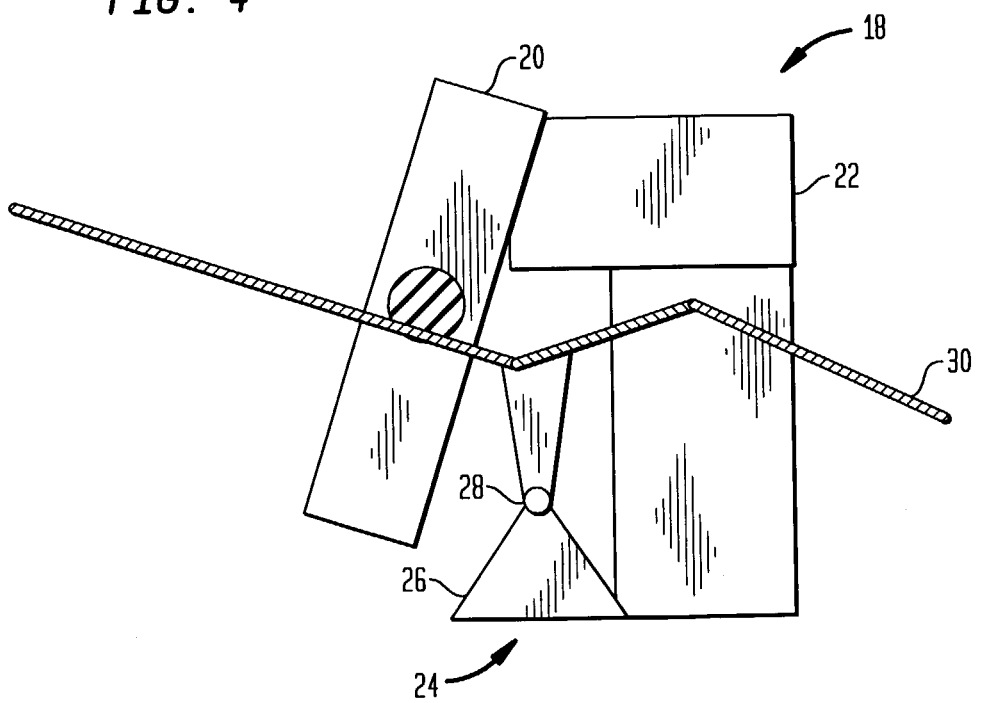
FIG. 4 is a side schematic view of the embodiment shown in FIG. 3 in a second position.

FIG. 4 shows the above embodiment of the present invention shown in FIG. 3 in such an imaging position. This position places the portion of the patient to be imaged within the field of view of the gamma camera within detector 20. A braking mechanism may be used with pivot 28 to fix the patient chair 30 in the appropriate loading and imaging positioning. Note that the exact positions that need to be created by the angle of pivot 28, for loading and imaging, will depend on the position of the gantry 22, and the patient's dimensions.

Figure 5:
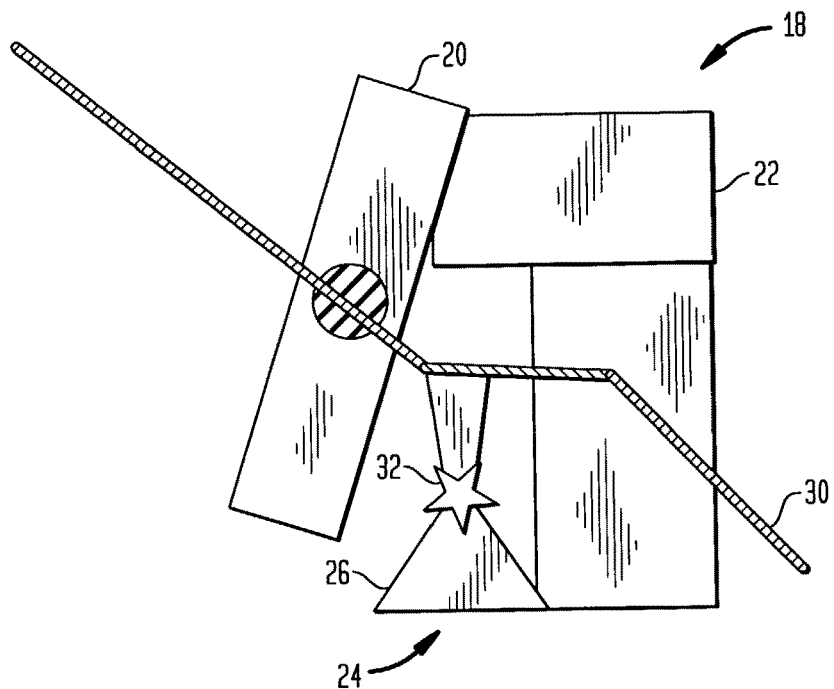
FIG. 5 is a side schematic view of another embodiment of the present invention.

FIG. 5 shows another embodiment of the present invention. Note that like numbers indicate like elements. This embodiment shows a motor driven joint 32. In operation, this allows for faster and easier patient loading and imaging than a manually driven joint.

Figure 6:
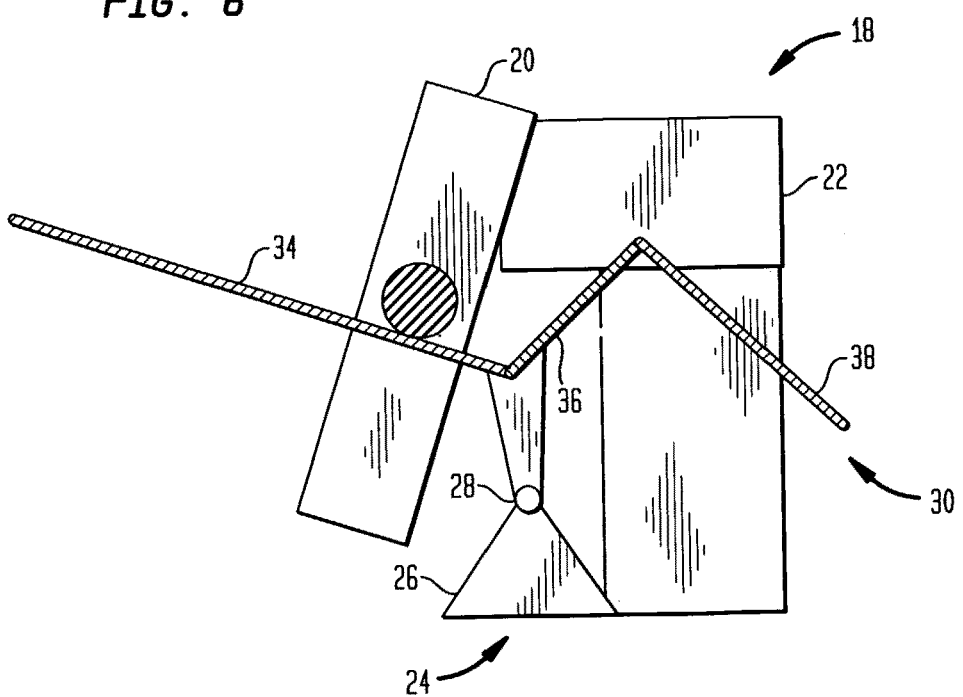
FIG. 6 is a side schematic view of another embodiment of the present invention.

FIG. 6 shows another embodiment of the present invention. The patient chair 30 is shown having a chair back 34, a chair seat 36 and a leg support 38. While the patient chair may have any form capable of supporting a patient in the loading and imaging positions, certain conformations of the patient chair may be more advantageous. Specifically, it is often advantageous that a patient have his knees bent in order be more comfortable while remaining still during the length of a scan. FIG. 6 shows a conformation giving this advantage with a back angle between chair back 34 and chair seat 36, and a leg angle between chair seat 36 and a leg support 38. The patient support 18 is shown in an imaging position to illustrate the relative positions of the patient's head and feet.

Figure 7:
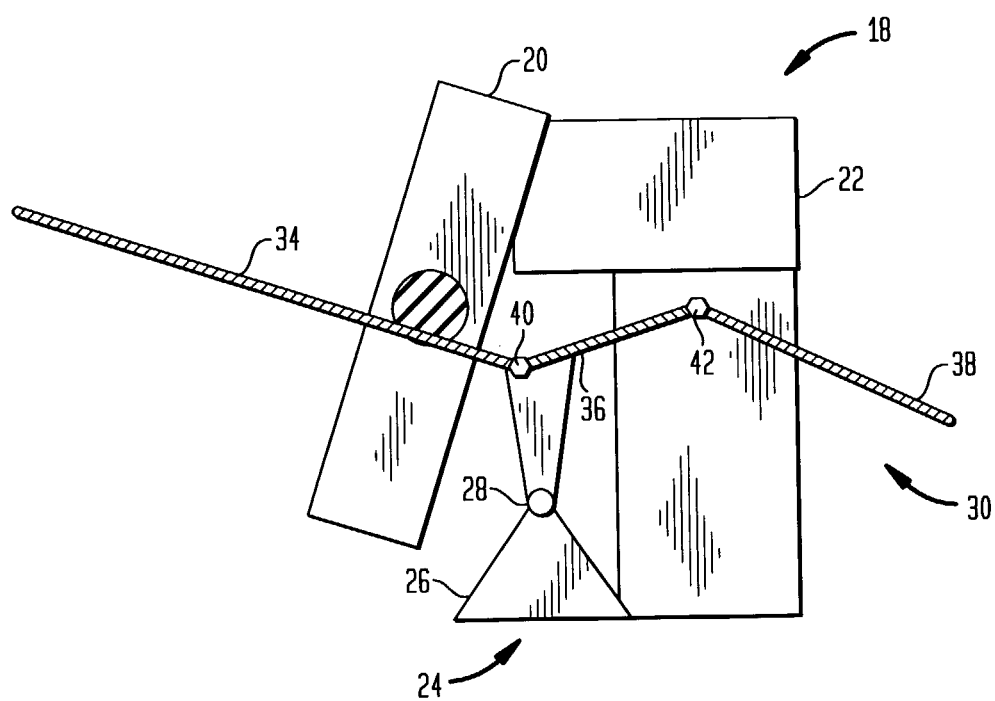
FIG. 7 is a side schematic view of another embodiment of the present invention.

FIG. 7 shows another embodiment of the present invention. First hinge 40 connects chair back 34 and chair seat 36, and a second hinge 42 connects chair seat 36 and a leg support 38. Thus the back angle between chair back 34 and chair seat 36 may be adjusted, and the leg angle between chair seat 36 and leg support 38 may be adjusted. An optimal conformation for individual patient comfort and imaging efficacy may therefore be set.

Figure 8:
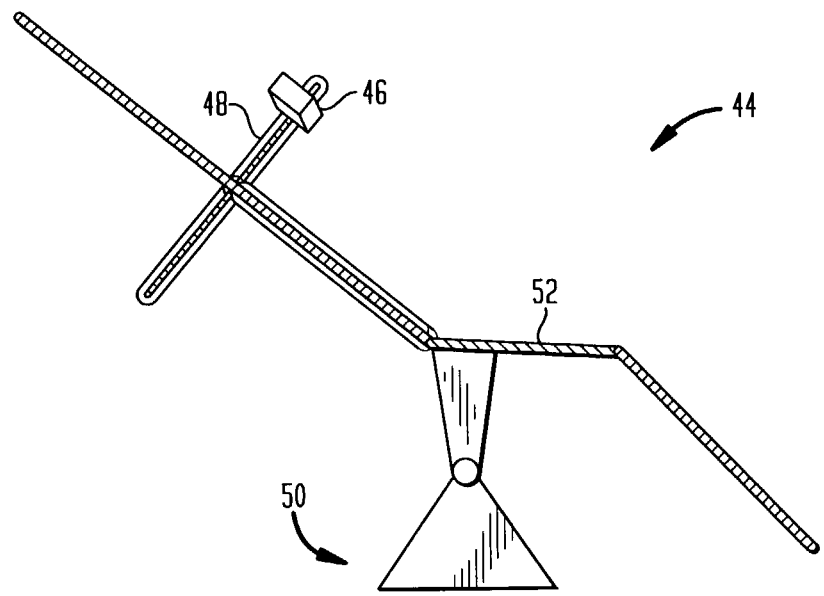
FIG. 8 is a side view of another embodiment of the present invention in a second position.

FIG. 8 shows another embodiment of the present invention. The nuclear medicine imaging system 44 has a detector 46 that is mounted on gantry 48, the gantry 48 itself being fixed to the patient support 50. Thus, the detector 46 moves with the gantry 48. Imaging in both the upright and reclining positions of patient support 50 is relatively easy to perform in this embodiment. The upright imaging position is particularly useful if the detector uses lighter weight and size technology, such as solid-state radiation detectors. Solid-state detectors, using materials such as Cadmium Zinc Telluride (CZT), directly convert gamma-ray radiation into measurable electric current. Alternatively, a smaller than conventional detector may use a standard scintillation crystal such as NaI with a solid-state photodiode.

However, generally note that for cardiac imaging in nuclear medicine a detector in an imaging position will usually be at right angles to the patient to optimize image quality.

A detector 46 allows for many more options in terms of potential fields of view for the gamma camera within detector 46. However, such a detector 46 may be in the way of patient chair 52 when it is moved from loading to imaging position. Therefore, the detector 46 may have to be moved to a loading position to allow patient access to the patient chair 52 and to allow the patient chair 52 to be moved into imaging position. Then the detector 46 may be moved into an imaging position, as shown in FIG. 9.

Figure 9:
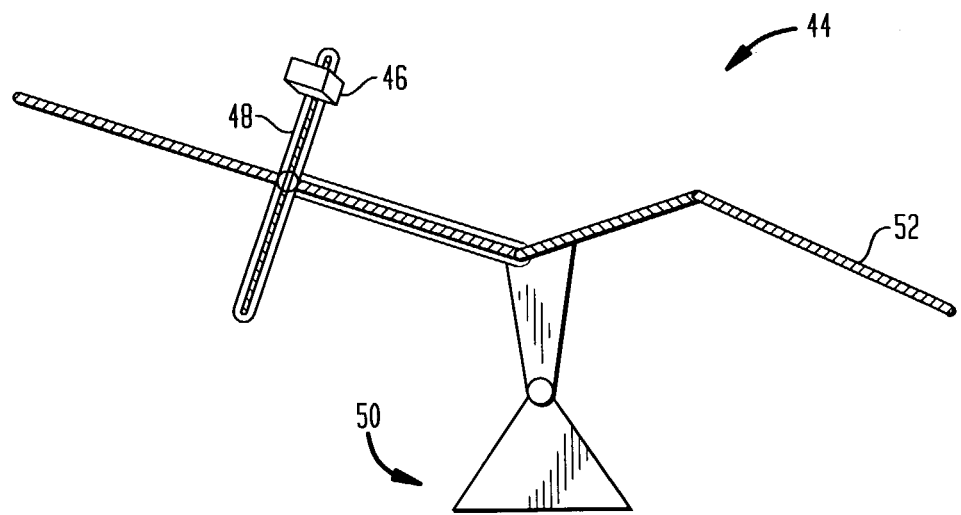
FIG. 9 is a side view of the embodiment of FIG. 8 in a second position.

Note that FIGS. 8 and 9 show a detector 46 and gantry 48 with specific degrees or dimensions of freedom. However, any degree of freedom may be incorporated into the gantry 48 and detector 46.

Figure 10:
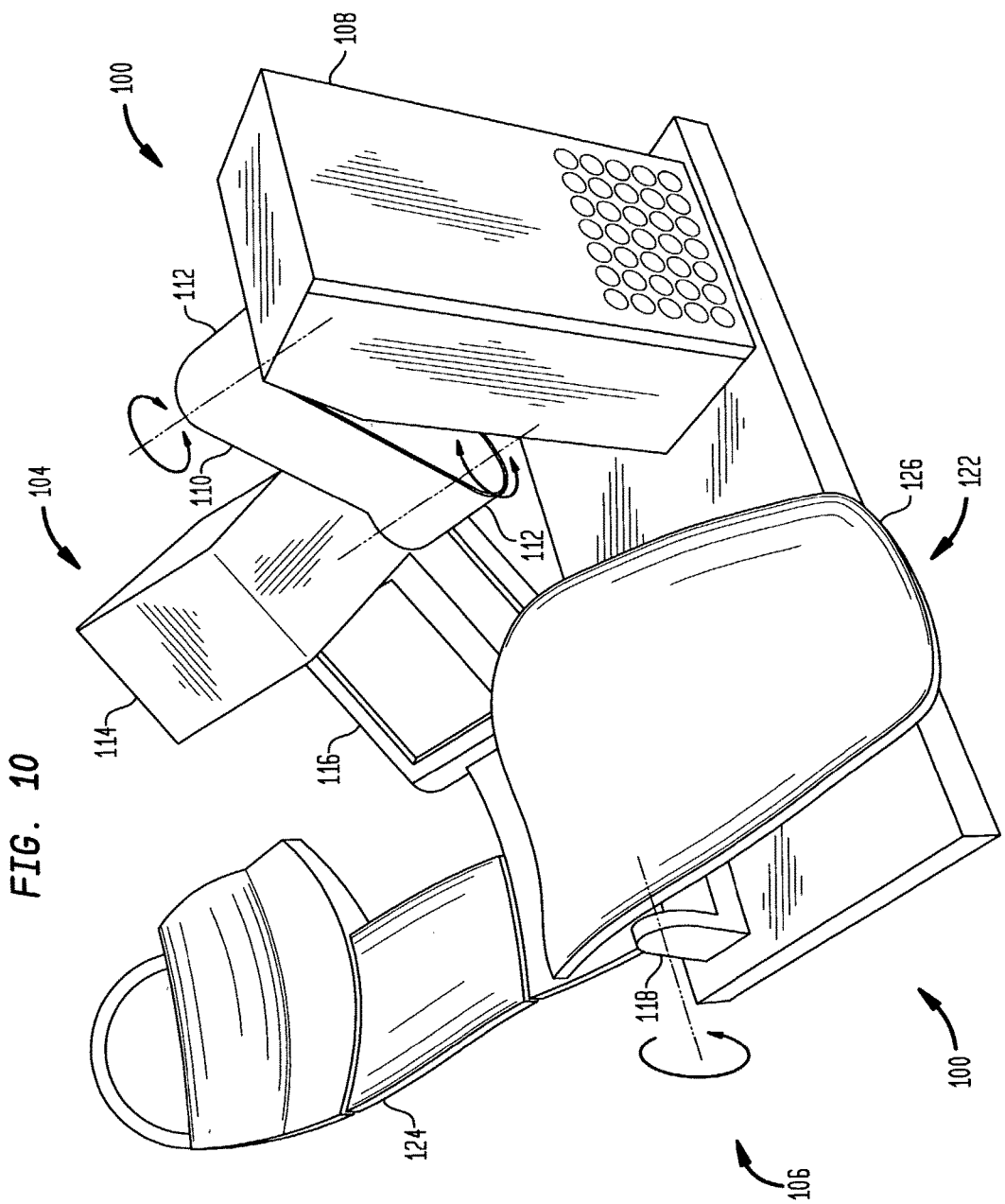
FIG. 10 is a perspective view of another embodiment of the present invention.
Figure 11:
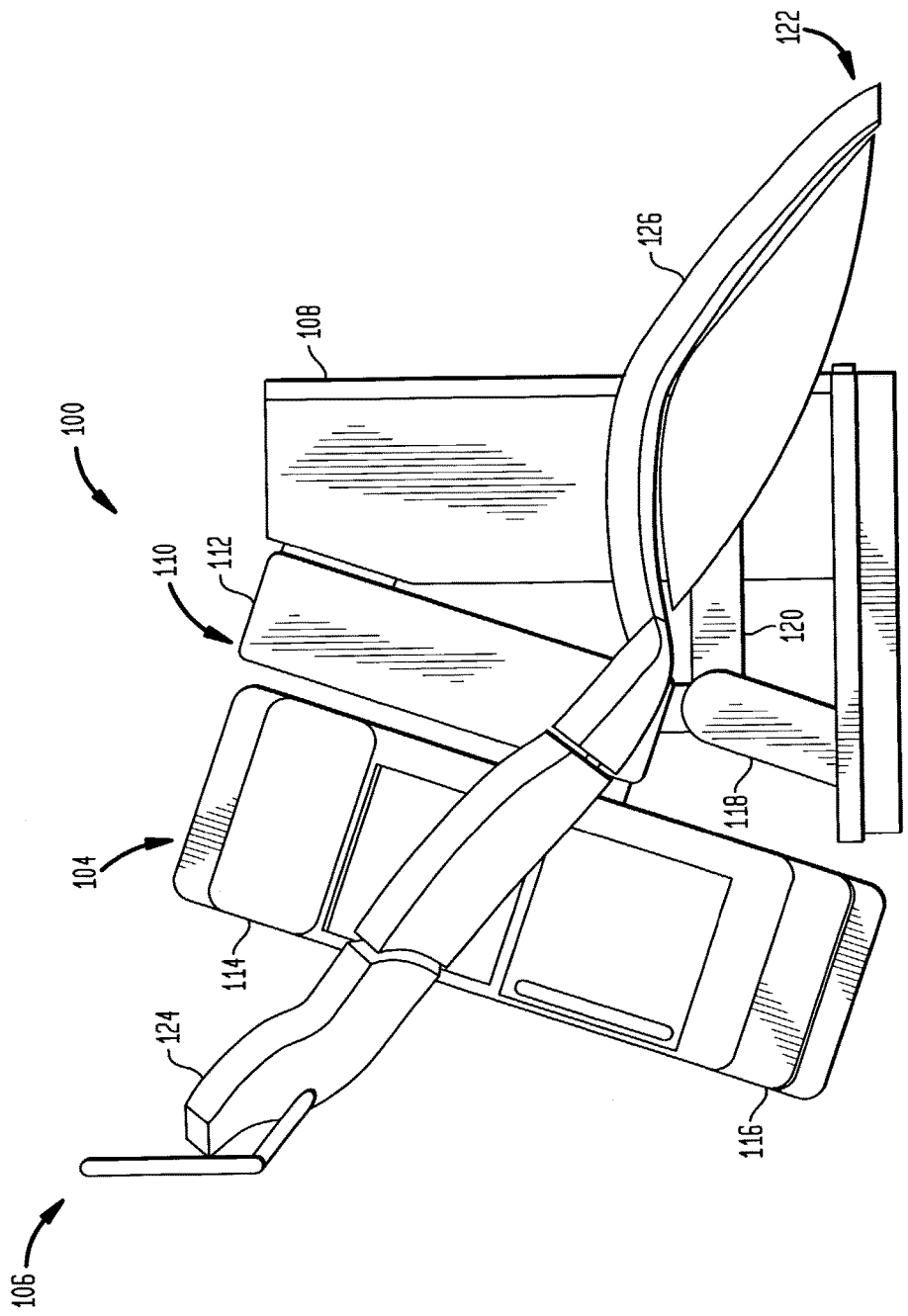
FIG. 11 is a side view of the embodiment shown in FIG. 9.

FIGS. 10-11 show another embodiment of the present invention. Nuclear imaging system 100 includes gantry 102, detector 104 and patient support 106. The gantry 102 includes a base unit 108 and an armature 110. The base unit 108 may move toward and away from the patient support 106. The first end 112 of the armature 110 is mounted to the base 108 such that the armature 110 may rotate. The second end 112 of the armature 110 is mounted to the detectors 104 such that the detectors 104 may also rotate. These three freedoms of movement allow the detectors 104 to be placed at any needed height and distance from the patient.

The detector 104 is shown including a detector 114 and a detector 116. This allows both better resolution than that of a single detector. Moreover, coincidence imaging becomes possible.

The patient support 106 itself includes a base, a pivot 118 mounted to the patient support base, a Y-beam support 120, and a patient chair 122. The patient chair 122 may rotate about pivot 118. The chair 122 includes a contoured back 124 and a contoured seat 126. Underneath the contoured seat 126 is contoured seat support 128 (see FIG. 12).

Figure 12:
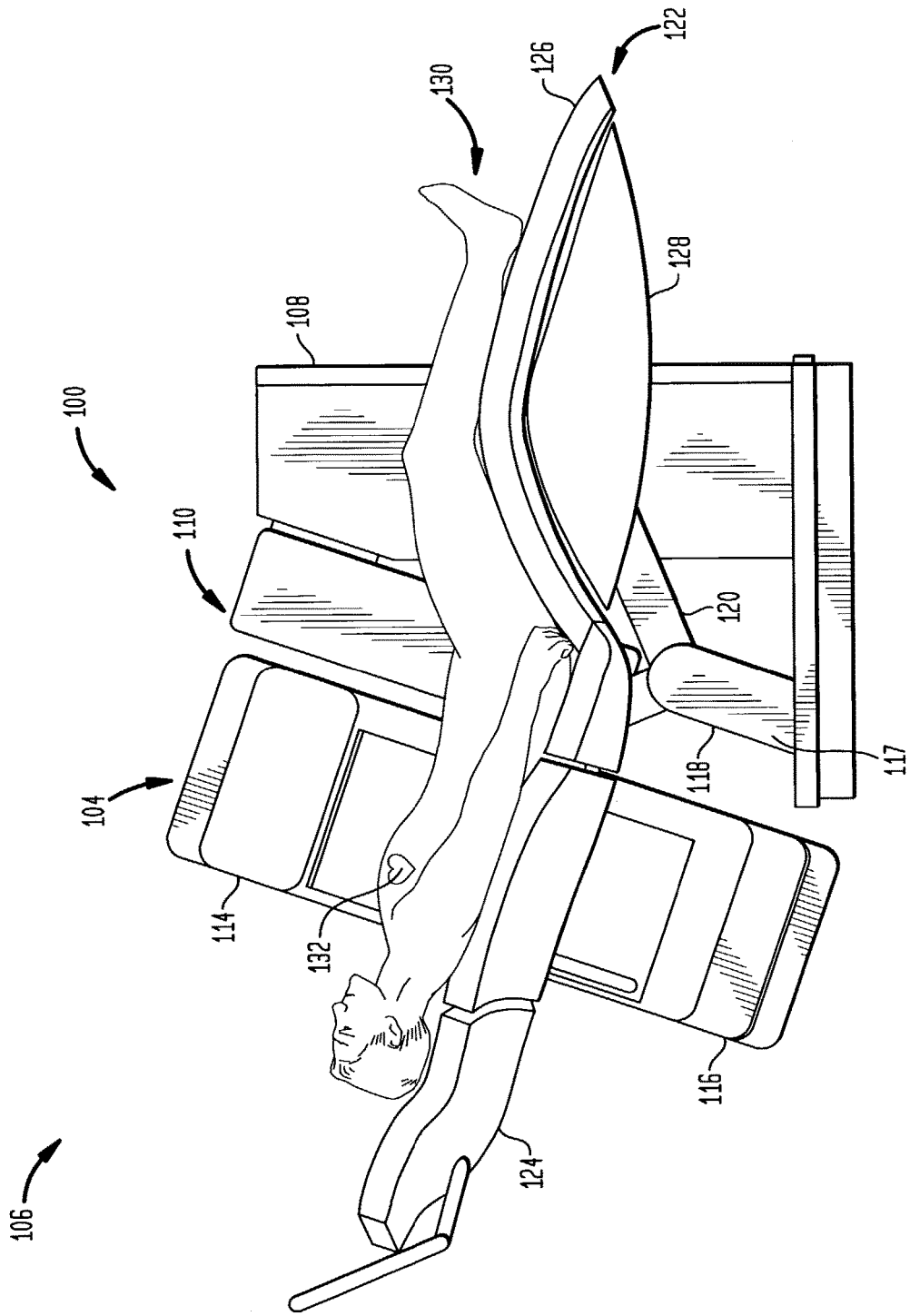
FIG. 12 is a side view of the embodiment shown in FIG. 9 in a loading position.

FIGS. 10-11 show the patient chair 122 in a loading position. FIG. 12 shows the patient chair 122 in an imaging position with a patient 130 outlined to clarify the operation of the nuclear imaging system 100. The patient region 132 is shown as the patient's cardiac region, a very common region to image. However, any region of the patient could be imaged in the same way as described herein.

In the imaging position, as opposed to the loading position, the patient's feet 134 are level with the patient's cardiac region 132. This is often advantageous in imaging a cardiac region.

Figure 13:
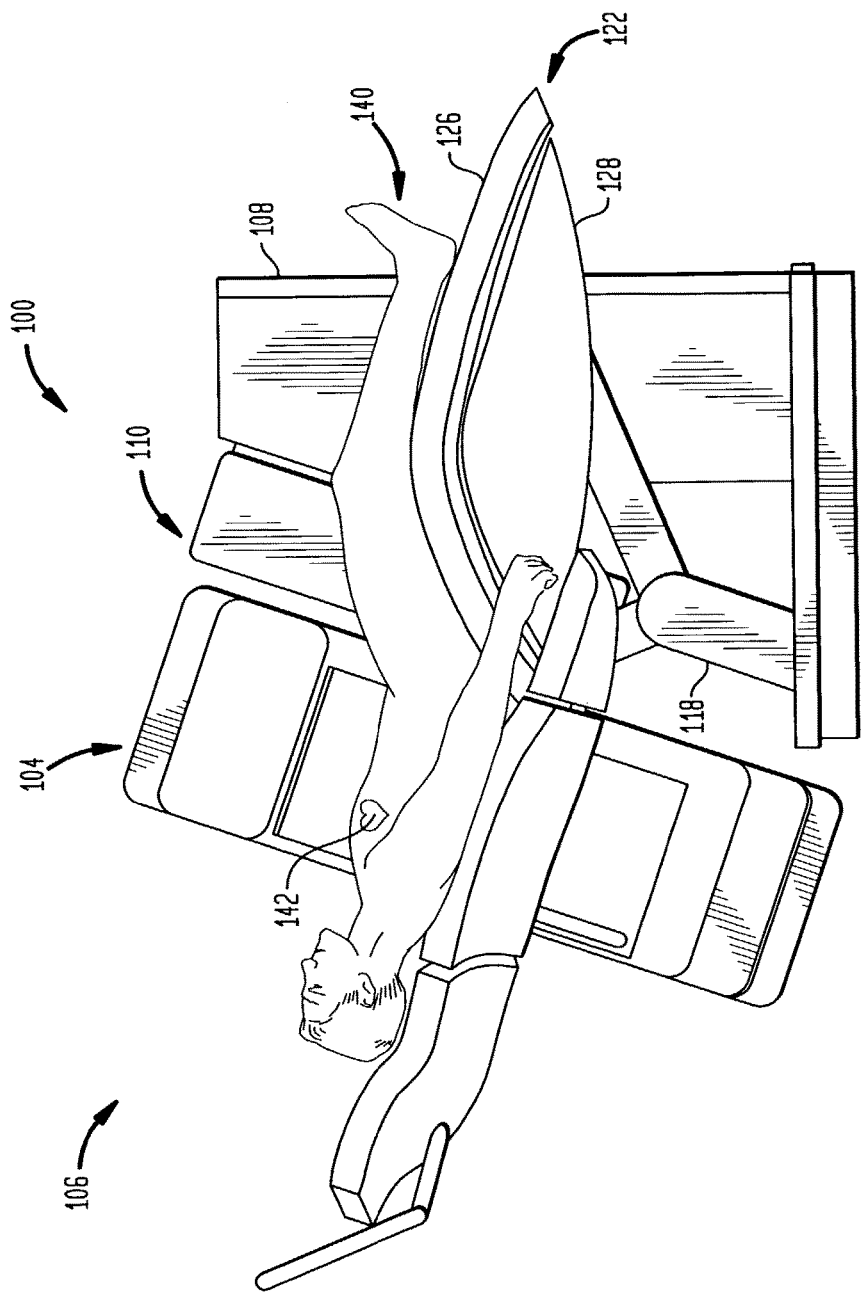
FIG. 13 is a side view of the embodiment shown in FIG. 9 in an imaging position.

FIG. 13 shows a patient 140, shorter than patient 130, in an imaging position in patient chair 122. The difference between FIG. 12 and FIG. 13 illustrates a direction of freedom of movement of the chair 122. In order to place patient region 142 in the field of view of the detectors 14, the contoured seat 126 has been moved up relative to the head of patient 140. Thus, patients of different size may be moved up and down to allow the imaging of the appropriate patient region. The seat support 128 may contain a motor or actuator in order to move the patient seat 126.

Each of the above embodiments allows a patient to be loaded into a patient support in a loading position and then imaged in a patient support in an imaging position. This is advantageous in allowing for optimum loading ease and minimum loading time, while allowing for an optimum imaging position for image quality.

The construction of the embodiments shown in FIGS. 3-12 by techniques and using materials that are well known in the art of nuclear medicine scanner systems, and imaging systems in general.

The patient support and imaging systems contemplated herein above may be applied beyond the nuclear medicine modality to other imaging modalities, such as Magnetic Resonance imaging (MRI) and Computerized Tomography (CT), in cases where these modalities are using an seated imaging position different from an easily loaded position of a patient support.

As these and other variations and combinations of the features discussed above can be utilized, the foregoing description of the preferred embodiments should be taken by way of illustration rather than by limitation of the invention set forth in the claims.

What is claimed is:

1. A nuclear radiation imaging system comprising:
    a patient support having a patient chair, a base, and a joint connected at one end to the base and at the other end to the patient chair, said patient chair having a relatively vertical loading position from which a patient is loaded into said patient chair, and a relatively horizontal imaging position for imaging of a patient loaded into said patient chair, wherein said patient chair pivots about said joint from said relatively vertical loading position to said relatively horizontal imaging position after said patient has been loaded into said patient chair from said relatively vertical loading position;
    a pair of nuclear radiation detectors mounted at right angles to each other; and
    a gantry including a base unit and an armature, a first end of the armature being rotationally mounted to the base unit such that the armature may rotate with respect to the base unit, a second end of the armature being mounted to said pair of nuclear radiation detectors such that said pair of nuclear detectors may rotate with respect to the armature, and said base unit being mounted to said base and being movable toward and away from said patient chair;
    said pair of nuclear radiation detectors being movably mounted to the gantry such that the pair of nuclear radiation detectors may be moved from a patient loading position enabling a patient to be loaded into said patient chair while in said relatively vertical loading position, wherein said patient loading position of said pair of nuclear radiation detectors does not enable imaging of a patient, to a patient imaging position enabling a patient to be imaged by said pair of nuclear radiation detectors,
    wherein said patient imaging position of said pair of nuclear radiation detectors does not enable loading of a patient into said patient chair from said relatively vertical loading position.

2. The imaging system of claim 1, wherein the patient chair comprises a back;
    a seat attached to the back at a back angle;
    a leg support attached to the seat at a leg angle;
    wherein said back and leg angles are optimized for patient comfort.

3. The imaging system of claim 2, wherein the patient chair further comprises:
    a back hinge connecting the back and the seat at the back angle;
    a leg hinge connecting the leg support and the seat at the leg angle;
    wherein the back hinge and the leg hinge may rotate to change the back angle and the leg angle.

4. The imaging system of claim 2, wherein the patient chair comprises:
    a back having a top edge and a bottom edge;
    a seat having a top edge and a bottom edge held next to the back at an angle;
    wherein the seat may move such that the top edge of the seat moves away from the bottom edge of the back and towards the top edge of the back.

5. The imaging system of claim 4, wherein the seat is contoured to hold the legs of a patient at an angle.

6. The imaging system of claim 5 wherein a seat supporter holds the seat and connects to the joint such that the seat supporter may actuate the movement of the seat.

7. The imaging system of claim 1, wherein said imaging of said patient comprises nuclear cardiology imaging.

8. A method of performing nuclear radiation imaging of a patient, comprising:
    loading a patient into a patient chair of a patient support, said patient support having a base and a joint connected at one end to the base and at the other end to the patient chair, wherein said patient is loaded into said patient chair at a relatively vertical loading position;
    moving the patient chair and patient from said relatively vertical loading position to a relatively horizontal imaging position for imaging of said patient, wherein said patient chair is pivoted about said joint from said relatively vertical loading position to said relatively horizontal imaging position after said patient has been loaded into said patient chair from said relatively vertical loading position;
    moving a pair of nuclear radiation detectors being mounted to a gantry at right angles to each other, said gantry including a base unit and an armature, a first end of the armature being rotationally mounted to the base unit such that the armature may rotate with respect to the base unit, a second end of the armature being mounted to said pair of nuclear radiation detectors such that said pair of nuclear detectors may rotate with respect to the armature, and said base unit being mounted to said base and being movable toward and away from said patient chair, said pair of nuclear radiation detectors being moved from a patient loading position enabling a patient to be loaded into said patient chair while in said relatively vertical loading position, wherein said patient loading position of said pair of detectors does not enable imaging of a patient, to a patient imaging position enabling a patient to be imaged by said pair of detectors, after said patient chair and patient have been moved from said relatively vertical loading position to said relatively horizontal imaging position; and
    imaging said patient with said pair of nuclear radiation detectors while said patient chair and patient are in said relatively horizontal imaging position and said pair of detectors are in said patient imaging position.

9. The method of claim 8, wherein said imaging of said patient comprises nuclear cardiology imaging.

* * * * *